(12) United States Patent
Bordier et al.

(10) Patent No.: US 6,660,284 B2
(45) Date of Patent: Dec. 9, 2003

(54) ANTHRAQUINONE COMPOUNDS, MANUFACTURING PROCESS, USE AS PIGMENTS AND COSMETIC COMPOSITION

(75) Inventors: Thierry Bordier, Tremblay-en-France (FR); Michel Philippe, Wissous (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/118,453

(22) Filed: Apr. 9, 2002

(65) Prior Publication Data

US 2003/0055273 A1 Mar. 20, 2003

(30) Foreign Application Priority Data

Apr. 11, 2001 (FR) .............................. 01 04989

(51) Int. Cl.[7] .............................. A61K 7/00; A61K 7/42; A61K 31/17; C07C 49/675; C07C 50/18
(52) U.S. Cl. ..................... 424/401; 424/400; 424/59; 552/218; 552/219; 514/580; 514/588; 514/844
(58) Field of Search ................. 552/218, 219; 424/400, 401, 59; 514/580, 588, 844

(56) References Cited

U.S. PATENT DOCUMENTS

| 5,486,629 A | 1/1996 | Chan et al. ................. 552/236 |
| 5,504,227 A | * 4/1996 | Lehmann et al. ........... 552/219 |

FOREIGN PATENT DOCUMENTS

| DE | 212 436 | 8/1909 |
| FR | 2 039 381 | 1/1971 |
| FR | 2 125 026 | 9/1972 |
| FR | 2 330 742 | 6/1977 |

* cited by examiner

*Primary Examiner*—Barbara P. Badio
(74) *Attorney, Agent, or Firm*—Steptoe & Johnson LLP; D. Douglas Price

(57) ABSTRACT

The present invention relates to novel compounds corresponding to formula (I) below:

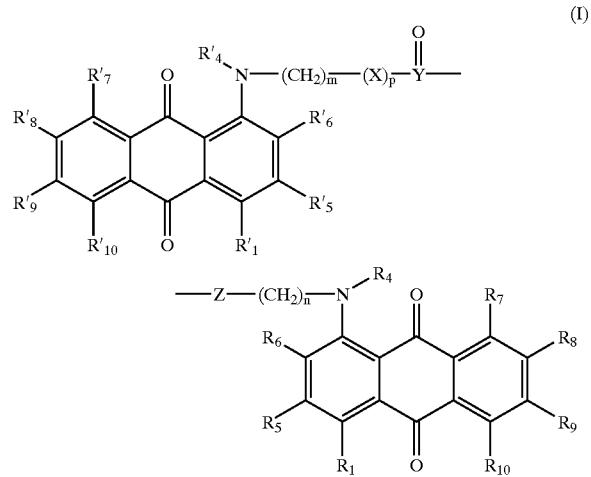

The invention also relates to the process for manufacturing them, to their use as pigments and to a cosmetic composition comprising them.

22 Claims, No Drawings

ANTHRAQUINONE COMPOUNDS, MANUFACTURING PROCESS, USE AS PIGMENTS AND COSMETIC COMPOSITION

The invention relates to a novel family of anthraquinone compounds, to a process for manufacturing them and to their use as pigments, especially in cosmetics. The invention is also directed toward cosmetic compositions containing them.

In the literature, the synthesis of colorants with an anthraquinone nucleus, in particular those substituted with amines, is well known. One synthesis is especially described in FR 2 039 381. Some of these colorants, such as those described in U.S. Pat. No. 5,486,629, are used for dyeing the hair.

These colorants are generally soluble in water or in apolar media (organic solvents and oils). They therefore cannot be used as insoluble pigments in applications such as skin makeup, since a leaching phenomenon is observed.

Consequently, this family of colorants has very little potential for industrial development as pigments, although certain polymerization processes, for instance the one described in U.S. Pat. No. 4,279,662, or complex treatment processes such as the one described in FR 2 060 730, have attempted to improve this persistent problem.

The inventors have discovered a novel family or anthraquinone compounds containing urea bonding which may be used as pigments, in particular in cosmetic compositions. These compounds, which are the subject of the invention, are insoluble or very sparingly soluble in aqueous media, and also in organic solvents and oily media. They may thus solve the problem of leaching observed with the anthraquinone colorants of the prior art in these media, and in particular in oily media.

In addition, these novel compounds are very accessible since they are prepared in a single step that is easy to carry out.

One subject of the present invention is thus novel anthraquinone compounds of formula (I) below.

Another subject of the invention is a process for manufacturing these novel compounds.

Yet another subject of the invention is the use of these compounds as pigments, especially in cosmetics.

A subject of the invention is also cosmetic compositions containing them.

Other subjects, characteristics, aspects and advantages of the invention will emerge even more clearly on reading the description and the various examples that follow.

According to the invention, the novel compounds correspond to the general formula (I):

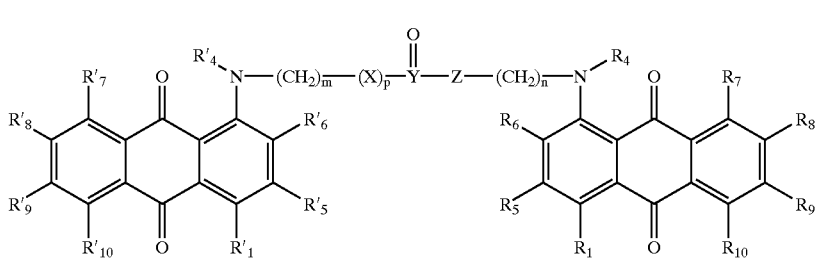

in which:

m and n, which may be identical or different, are between 1 and 20;

X and Z each represent NH or O;

p is 0 or 1;

Y represents a carbon atom or a sulphur atom;

$R_1$, $R'_1$, $R_5$, $R'_5$, $R_6$, $R'_6$, $R_7$, $R'_7$, $R_8$, $R'_8$, $R_9$, $R'_9$, $R_{10}$ and $R'_{10}$, which may be identical or different, each represent a hydrogen atom, a halogen atom, a linear or branched, saturated or unsaturated $C_{1-8}$ hydrocarbon-based group, a hydroxyl group,

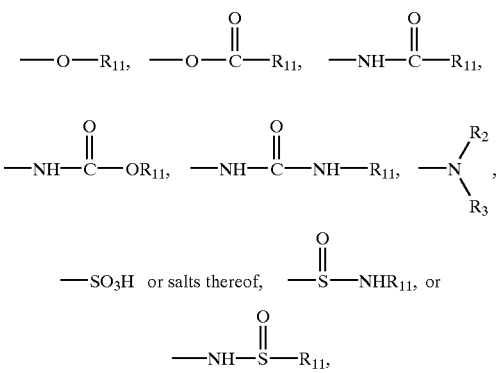

and $R_2$, $R_3$, $R_4$, $R'_4$ and $R_{11}$, which may be identical or different, each represent a hydrogen atom, a linear or branched, saturated or unsaturated, optionally hydroxylated, $C_{1-8}$ hydrocarbon-based group.

The hydrocarbon-based groups that are suitable in the present invention are linear or branched, saturated or unsaturated and contain from 1 to 8 carbon atoms and preferably from 1 to 4 carbon atoms.

Hydrocarbon-based groups that may especially be mentioned include alkyl, alkenyl or alkynyl groups such as, for example, methyl, ethyl, n-propyl, isopropyl, n-butyl, isobutyl, tert-butyl, methylene, ethenyl or ethynyl groups.

Halogen atoms that may especially be mentioned include chlorine, bromine, fluorine and iodine atoms, and preferably the chlorine atom.

The preferred compounds of the invention are those corresponding to formula (I) in which n=m, $R'_1=R_1$, $R'_4=R_4$, $R'_5=R_5$, $R'_6=R_6$, $R'_7=R_7$, $R'_8=R_8$, $R'_9-R_9$ and $R'_{10}=R_{10}$, Z=X and p=1, and the compounds that are more particularly preferred correspond to the general formula (II) below:

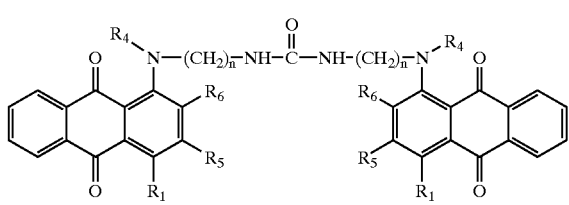

(II)

in which:
n is from 1 to 12,
$R_1$ represents a hydrogen atom, a halogen atom, a linear or branched, saturated or unsaturated $C_1$–$C_8$ hydrocarbon-based group, a hydroxyl group or a group —$NR_2R_3$,
$R_2$, $R_3$ and $R_4$ each represent a hydrogen atom or a linear or branched, saturated or unsaturated $C_1$–$C_8$ hydrocarbon-based group, and
$R_5$ and $R_6$ each represent a hydrogen atom, a halogen atom, a linear or branched, saturated or unsaturated $C_1$–$C_8$ hydrocarbon-based group or a hydroxyl group.

Examples of compounds of formula (I) or (II) above that may especially be mentioned include 1,3-bis[3-(9,10-dioxo-9,10-dihydroanthracen-1-ylamino)propyl]urea and 1,3-bis[3-(4-methylamino-9,10-dioxo-9,10-dihydro-anthracen-1-ylamino)propyl]urea.

Another subject of the present invention is the process for manufacturing the compounds of formula (I) above.

This process consists in reacting an anthraquinone derivative of general formula (III) with an anthraquinone derivative of general formula (IV):

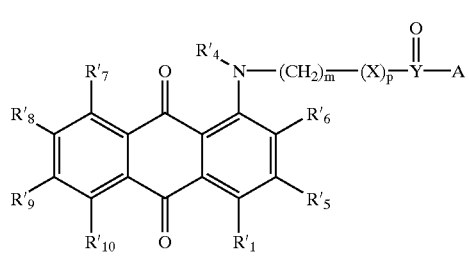

(III)

in which A represents an activating group such as, especially, a group derived from imidazole or a halogen atom, the other symbols having the same meaning as for formula (I);

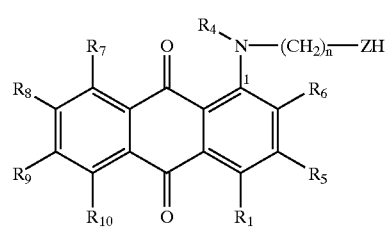

(IV)

in which $R_1$, $R_4$ to $R_{10}$, Z and n have the same meaning as for formula (I)
in the presence of a solvent and optionally a base, at a temperature from 0 to about 160° C. for about 30 minutes to about 20 hours.

The solvents that are suitable in the present invention are preferably dipolar aprotic solvents such as, for example, N,N-dimethylacetamide or N,N-dimethyl-formamide.

The bases that may be used are especially chosen from pyridine or its derivatives, triethylamine and diisopropylethylamine.

One preferred manufacturing process of the invention makes it possible to obtain compounds of formula (I) above in which $R'_1=R_1$, $R'_4=R_4$, $R'_5=R_5$, $R'_6=R_6$, $R'_7=R_7$, $R'_8=R_8$, $R'_9=R_9$ and $R'_{10}=R_{10}$, n=m, Z=X and p=1. It makes it possible, inter alia, to obtain the particularly preferred compounds of formula (II) above.

The process consists in reacting an anthraquinone derivative of general formula (IV):

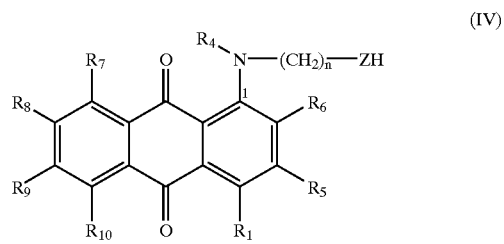

(IV)

in which n, Z, $R_1$ and $R_4$ to $R_{10}$ are as defined above for formula (I), or one of its salts,
with phosgene or one of its derivatives or of its substitutes, or instance carbonyldiimidazole, at a temperature from 0 to about 160° C. for about 30 minutes to about 20 hours in the presence of a solvent as defined above, and optionally of a base as described above.

The invention also relates to the use as a pigment of at least one compound of formula (I) or (II) as defined above, and preferably 1,3-bis[3-(9,10-dioxo-9,10-dihydroanthracen-1-ylamino)propyl]urea and 1,3-bis[3-(4-methylamino-9,10-dioxo-9,10-dihydroanthracen-1-ylamino)propyl]urea.

This novel family of pigments may be used in the food and cosmetics sectors and in paints, and preferably in cosmetics.

The cosmetic composition according to the invention comprises, in a cosmetically acceptable medium, at least one compound of formula (I) or (II) as defined above. This compound is especially present in an amount of between 0.01% and 50% by weight and preferably between 0.1% and 25% by weight relative to the total weight of the composition.

The expression "cosmetically acceptable medium" means a medium that is compatible with all keratin materials such as the skin, the nails, the hair, the eyelashes, the eyebrows and the lips, and any other area of body or facial skin.

The medium may comprise or be in the form of, for example, a suspension, a dispersion, a solution in a solvent or an aqueous-alcoholic medium, optionally thickened or even gelled; an oil-in-water, water-in-oil or multiple emulsion; a gel or a mousse; an emulsified gel; a dispersion of vesicles, especially a lipid dispersion; a two-phase or multiphase lotion; a spray, a free, compact or cast powder; or an anhydrous paste.

A person skilled in the art may select the appropriate presentation form, and also the method for preparing it, on the basis of his general knowledge, taking into account firstly the nature of the constituents used, especially their solubility in the support, and secondly the intended application for the composition.

When the composition is in aqueous form, especially in the form of a dispersion, an emulsion or an aqueous solution, it can comprise an aqueous phase which comprises water, a floral water and/or mineral water.

The aqueous phase may also comprise alcohols such as $C_1$–$C_6$ monoalcohols and/or polyols such as glycerol, butylene glycol, isoprene glycol, propylene glycol or polyethylene glycol.

When the composition according to the invention is in the form of an emulsion, it can optionally also comprise a surfactant, preferably in an amount from 0.01% to 30% by weight relative to the total weight of the composition. The composition according to the invention may also comprise at least one co-emulsifier which may be chosen from oxyethylenated sorbitan monostearate, fatty alcohols such as stearyl alcohol or cetyl alcohol, or fatty acid esters of polyols such as glyceryl stearate.

The composition according to the invention may also comprise one or more thickeners in concentrations preferably ranging from 0 to 6% by weight relative to the total weight of the composition, chosen from:
(1) polysaccharide biopolymers, for instance xanthan gum, carob gum, guar gum, alginates, modified celluloses, starch derivatives, cellulose ether derivatives containing quaternary ammonium groups, and cationic polysaccharides;
(2) synthetic polymers, for instance poly(acrylic acid), polyvinylpyrrolidone, poly(vinyl alcohol) and acrylamide-based polymers; and
(3) magnesium aluminium silicate.

Depending on the intended application, the composition may also comprise a film-forming polymer. This is especially the case when it is desired to prepare a composition of the type such as a nail varnish, a mascara, an eyeliner or a hair care composition of the type such as a lacquer. The polymers may be dissolved or dispersed in the cosmetically acceptable medium. In particular, the polymer may be present in the form of a solution in an organic solvent or in the form of an aqueous dispersion of film-forming polymer particles. The polymer may be chosen from nitrocellulose, cellulose acetobutyrate, poly(vinyl butyrals), alkyd resins, polyesters, acrylic polymers, vinyl polymers and/or polyurethanes.

The composition may also comprise at least one plasticizer, which may be present in an amount ranging from 1% to 40% by weight relative to the total weight of the composition.

The composition according to the invention may also comprise a fatty phase, consisting especially of fatty substances that are liquid at 25° C., such as oils of animal, plant, mineral or synthetic origin; the fatty substances that are solid at 25° C., such as waxes of animal, plant, mineral or synthetic origin; pasty fatty substances; gums; or mixtures thereof.

The compositions according to the invention may thus comprise volatile oils, which will evaporate on contact with the skin, but whose presence in the cosmetic composition is useful since they make the composition easier to spread when it is applied to the skin. The volatile oils that are particularly suitable in the invention generally have, at 25° C., a saturating vapor pressure at least equal to 50 Pa (0.5 millibar).

Examples that may be mentioned include volatile silicone oils, such as:
(1) cyclic volatile silicones containing from 3 to 8 and preferably from 4 to 6 silicon atoms;
(2) cyclocopolymers of the dimethylsiloxane/methylalkylsiloxane type; and
(3) linear volatile silicones containing from 2 to 9 silicon atoms.

Mention may also be made of volatile hydrocarbon-based oils such as isoparaffins and especially isododecane and fluoro oils.

Non-volatile oils can also be used, among which mention may be made of:
(1) poly($C_1$–$C_{20}$)alkylsiloxanes and especially those containing trimethylsilyl end groups, among which mention may be made of linear polydimethylsiloxanes and alkylmethylpolysiloxanes such as cetyldimethicone (CTFA name);
(2) silicones modified with aliphatic and/or aromatic groups, which may be fluorinated, or with functional groups such as hydroxyl, thiol and/or amine groups;
(3) phenylsilicone oils, especially those of formula:

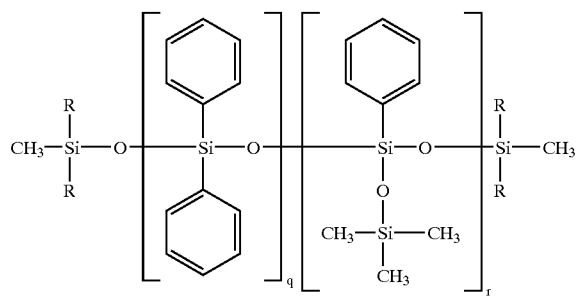

in which R represents a $C_1$–$C_{30}$ alkyl group, an aryl group or an aralkyl group, q is an integer between 0 and 100, and r is an integer between 0 and 100, with the proviso that the sum is between 1 and 100;
(4) oils of animal, plant or mineral origin, and especially animal or plant oils formed from fatty acid esters of polyols, in particular liquid triglycerides, for example sunflower oil, corn oil, soybean oil, marrow oil, grape seed oil, sesame oil, hazelnut oil, apricot oil, almond oil or avocado oil; fish oils, glyceryl tricaprocaprylate, or plant or animal oils of formula $R_a COOR_b$, in which $R_a$ represents a fatty acid residue containing from 7 to 19 carbon atoms and $R_b$ represents a branched hydrocarbon-based chain containing from 3 to 20 carbon atoms, for example, purcellin oil, liquid paraffin, liquid petroleum jelly, perhydrosqualene, wheat germ oil, beauty-leaf oil, sesame oil, macadamia oil, grape seed oil, rape seed oil, coconut oil, ground nut oil, palm oil, castor oil, jojoba oil, olive oil or cereal germ oil, fatty acid esters, alcohols, acetylglycerides, octanoates, decanoates or ricinoleates of alcohols or of polyalcohols, fatty acid triglyercides and glycerides; and
(5) fluoro oils and perfluoro oils.

The composition according to the invention may also comprise other fatty substances that may be chosen by a person skilled in the art on the basis of his general knowledge, so as to give the final composition the desired properties, for example in terms of consistency and/or texture. These additional fatty substances may be waxes, gums and/or pasty fatty substances of animal, plant, mineral or synthetic origin, and also mixtures thereof. Mention may be made especially of silicone gums, waxes of animal, plant, mineral or synthetic origin, such as microcrystalline waxes, paraffin, petrolatum, petroleum jelly, ozokerite or montan wax; beeswax, lanolin and its derivatives; candelilla wax, ouricury wax, carnauba wax, Japan wax, cocoa butter, cork fibre wax or sugarcane wax; hydrogenated oils, ozokerites, fatty esters and glycerides, polyethylene waxes and the waxes obtained by Fischer-Tropsch synthesis, lanolins, silicone waxes, fluoro waxes and polyolefins.

The composition may also contain nacres and/or fillers, and also other pigments that are well known in the art.

The nacres may be present in the composition in a proportion of from 0 to 20% by weight and preferably from 8% to 15% by weight, and may be chosen from natural mother-of-pearl, mica coated with titanium oxide, with iron oxide, with natural pigment or with bismuth oxychloride, and also coloured titanium mica.

The fillers, which may be present in a proportion of from 0 to 30% by weight and preferably from 5% to 15%, in the composition, may be mineral or synthetic, and lamellar or non-lamellar. Mention may be made of talc, mica, silica, kaolin, nylon powder, polyethylene powder, Teflon, starch, boron nitride, polymer microspheres such as Expancel® (Nobel Industrie), Polytrap® (Dow Corning) and silicone resin microbeads (for example Tospearls® from Toshiba), precipitated calcium carbonate, magnesium carbonate, magnesium hydrocarbonate and metal soaps derived from organic carboxylic acids containing from 8 to 22 carbon atoms.

The composition may also comprise a water-soluble or liposoluble colorant, especially a natural organic colorant such as cochineal carmine, and/or a synthetic colorant such as halo acid dyes, azo dyes or anthraquinone dyes. Mention may also be made of mineral colorants such as copper sulphate.

The composition may also comprise any additive usually used in cosmetics, such as fragrances, essential oils, preserving agents, lipophilic or hydrophilic cosmetic active agents, moisturizers, vitamins, essential fatty acids, sphingolipids, self-tanning agents such as dihydroxyacetone (DHA), sunscreens, antifoams, sequestering agents, antioxidants and dispersants.

Needless to say, a person skilled in the art will take care to select the optional additional compound(s) mentioned above, such that the advantageous properties intrinsically associated with the composition according to the invention are not, or are not substantially, adversely affected by the envisaged addition(s).

The cosmetic compositions according to the invention may be:
(1) in the form of a makeup product for facial or body skin or the lips or keratin fibres (nails, eyelashes, eyebrows or hair), such as a foundation, a tinted cream, a face powder, an eye shadow, a free or compact powder, a concealer stick, a cover stick, an eyeliner, a mascara, a lipstick, a nail varnish or a hair makeup composition;
(2) in the form of a skin care product for the face or the body including the scalp, such as a facial care composition (day product, night product, anti-wrinkle product, moisturizing product, etc.) or a matt-effect composition for the face;
(3) in the form of an antisun composition or an artificial tanning (self-tanning) composition; or
(4) in the form of a hair composition, and especially a styling cream or gel, a dye composition or oxidation dye composition, optionally in the form of a coloring shampoo.

The examples that follow are intended to illustrate the invention and should not be considered in any way as limiting the invention.

EXAMPLE 1

Preparation of 1,3-bis[3-(9,10-dioxo-9,10-dihydroanthracen-1-ylamino)propyl]urea (Formula (II) with $R_1$, $R_4$, $R_5$, $R_6$=H and n=3)

5 g (17.84 mmol) of 1-[(3-aminopropyl)amino]-9,10-anthracenedione were partially dissolved at room temperature in 200 ml of dimethylformamide in a 250 ml three-necked flask, under a nitrogen atmosphere. 1.5 g (0.55 eq.) of carbonyldiimidazole were then added.

The mixture was then stirred for 1 hour at room temperature and then heated to 40° C. for 5 hours. After filtration, washing with water and acetone and then drying under vacuum at 50° C., 4.5 g of a dark red powder were obtained (final yield of 90%).

The characteristics of the final product are as follows:

melting point above 260° C. (measured on a Kofler block), mass spectrum (SSQ710, CI-DI): m/z=587, elemental analysis ($C_{35}H_{30}N_4O_5$, MW=586.653):

|  | C | H | N | O |
|---|---|---|---|---|
| % calculated | 71.66 | 5.15 | 9.55 | 13.64 |
| % found | 71.03 | 5.11 | 9.89 | 14.19 |

EXAMPLE 2

Preparation of 1,3-bis[3-(4-methylamino-9,10-dioxo-9,10-dihydroanthracen-1-ylamino)propyl]urea (Formula (II) with $R_4$, $R_5$ and $R_6$=H, $R_1$=NHCH$_3$ and n=3)

5 g (16.27 mmol) of 1-[(3-aminopropyl)amino]-9,10-anthracenedione were partially dissolved at room temperature in 200 ml of dimethylformamide in a 250 ml three-necked flask under a nitrogen atmosphere. 1.45 g (0.5 eq) of carbonyldiimidazole were then added.

The mixture was first stirred for 1 hour at room temperature and then heated at 40° C. for 6 hours. After filtration, washing with water and acetone and then drying under vacuum at 50° C., 3.9 g of a purple-blue powder were obtained (final yield of 73%).

The characteristics of the final product are as follows:

melting point above 260° C. (measured on a Kofler block), mass spectrum (SSQ710, EI-DEP): m/z=644, elemental analysis ($C_{37}H_{36}N_6O_5$, MW=644.7280):

|  | C | H | N | O |
|---|---|---|---|---|
| % calculated | 68.93 | 5.63 | 13.03 | 12.41 |
| % found | 67.91 | 5.56 | 13.03 | 12.94 |

Formulation Example No. 1
A tinted cream of oil-in-water emulsion type is prepared from the following ingredients:

| | |
|---|---|
| Parleam oil | 22 g |
| Stearic acid | 1.5 g |
| Polysorbate 60[(1)] (sold under the trade name Tween ® 60 by the company ICI) | 0.9 g |
| Cetyl alcohol | 0.5 g |
| Glyceryl monostearate/PEG 100 stearate mixture | 2.1 g |
| Triethanolamine | 0.75 g |
| Compound of Example 1 | 5 g |
| Propylene glycol | 3 g |
| Cyclopentadimethylsiloxane | 3 g |
| Carbopol 981 | 0.15 g |
| Xanthan gum | 0.2 g |
| Water | qs 100 g |

-continued

Formulation Example No. 2
An eye shadow is prepared from the following ingredients:

| | |
|---|---|
| Talc | 38 g |
| Mica | 20 g |
| Bismuth oxychloride | 8 g |
| Zinc stearate | 3 g |
| Nylon powder | 20 g |
| Compound of Example 2 | 5 g |
| Water | qs 100 g |

A stable blue eye shadow that has good cosmetic properties is obtained.

Formulation Example No. 3
A lipstick is prepared from the following ingredients:

| | |
|---|---|
| Polyethylene wax | 15 g |
| Compound of Example 1 | 10 g |
| Parleam oil | qs 100 g |

A lipstick with good cosmetic properties is obtained.

What is claimed is:

1. A compound having the formula (I):

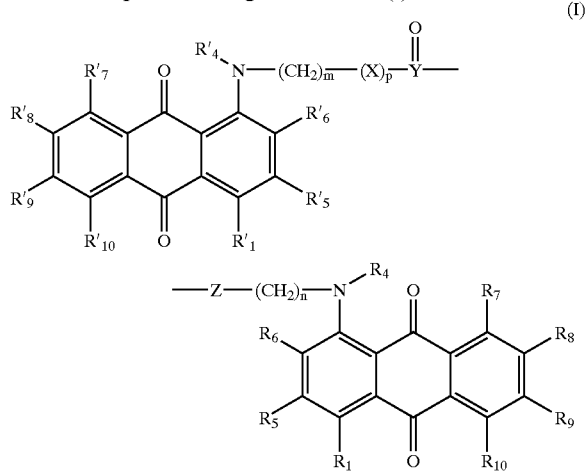

in which:
m and n, which may be identical or different, are between 1 and 20;
X and Z each represent NH or O;
p is 0 or 1;
Y represents a carbon atom or a sulphur atom;
$R_1$, $R'_1$, $R_5$, $R'_5$, $R_6$, $R'_6$, $R_7$, $R'_7$, $R_8$, $R'_8$, $R_9$, $R'_9$, $R_{10}$ and $R'_{10}$, which may be identical or different, each represent a hydrogen atom, a halogen atom, a linear or branched, saturated or unsaturated $C_{1-8}$ hydrocarbon-based group, a hydroxyl group,

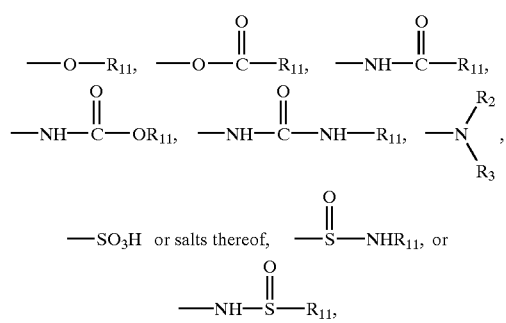

and $R_2$, $R_3$, $R_4$, $R'_4$ and $R_{11}$, which may be identical or different, each represent a hydrogen atom, a linear or branched, saturated or unsaturated, optionally hydroxylated, $C_{1-8}$ hydrocarbon-based group.

2. A compound having the formula (II):

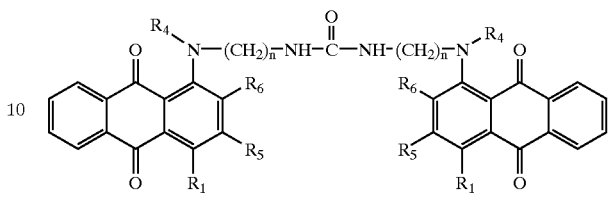

in which:
n is from 1 to 12;
$R_1$ represents a hydrogen atom, a halogen atom, a linear or branched, saturated or unsaturated $C_1$–$C_8$ hydrocarbon-based group, a hydroxyl group or a group —$NR_2R_3$;
$R_2$, $R_3$ and $R_4$ each represent a hydrogen atom or a linear or branched, saturated or unsaturated $C_1$–$C_8$ hydrocarbon-based group; and
$R_5$ and $R_6$ each represent a hydrogen atom, a halogen atom, a linear or branched, saturated or unsaturated $C_1$–$C_8$ hydrocarbon-based group or a hydroxyl group.

3. The compound according to claim 1, wherein the compound is 1,3-bis[3-(9,10-dioxo-9,10-dihydroanthracen-1-ylamino)propyl]urea or 1,3-bis[3-(4-methylamino-9,10-dioxo-9,10-dihydroanthracen-1-ylamino)propyl]urea.

4. A process for making the compound according to claim 1, wherein an anthraquinone derivative of formula (III) with an anthraquinone derivative of formula (IV):

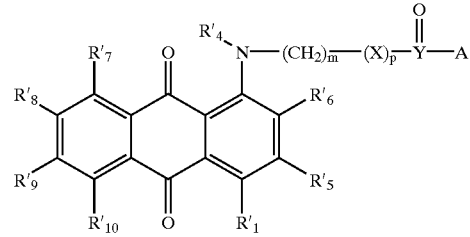

in which:
A represents an activating group,
m is between 1 and 20;
X represents NH or O;
p is 0 or 1;
Y represents a carbon atom or a sulphur atom;
$R'_1$, $R'_5$, $R'_6$, $R'_7$, $R'_8$, $R'_9$ and $R'_{10}$, which may be identical or different, each represent a hydrogen atom, a halogen atom, a linear or branched, saturated or unsaturated $C_{1-8}$ hydrocarbon-based group, a hydroxyl group,

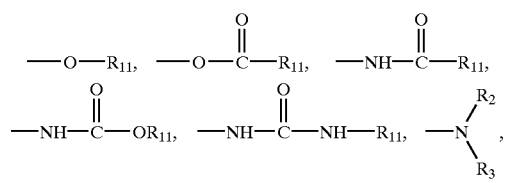

-continued

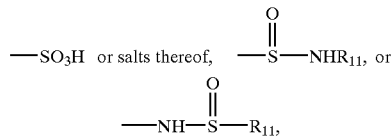

and $R_2$, $R_3$, $R'_4$ and $R_{11}$, which may be identical or different, each represent a hydrogen atom, a linear or branched, saturated or unsaturated, optionally hydroxylated $C_{1-8}$ hydrocarbon-based group; and

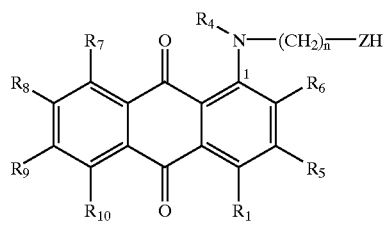

(IV)

in which:

n is between 1 and 20;

Z represents NH or O;

$R_1$, $R_5$, $R_6$, $R_7$, $R_8$, $R_9$ and $R_{10}$, which may be identical or different, each represent a hydrogen atom, a halogen atom, a linear or branched, saturated or unsaturated $C_{1-8}$ hydrocarbon-based group, a hydroxyl group,

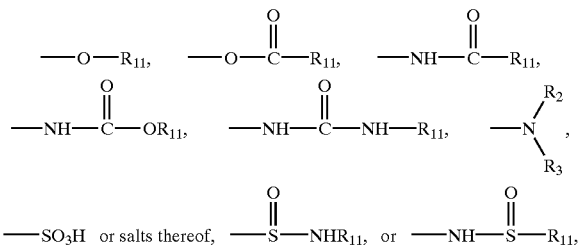

and $R_2$, $R_3$, $R_4$ and $R_{11}$, which may be identical or different, each represent a hydrogen atom, a linear or branched, saturated or unsaturated, optionally hydroxylated $C_{1-8}$ hydrocarbon-based group;

are reacted together in the presence of a solvent and optionally a base at a temperature from 0 to about 160° C. for about 30 minutes to about 20 hours.

5. The process according to claim 4, wherein A represents an activating group derived from imidazole or a halogen atom.

6. A manufacturing process comprising reacting an anthraquinone derivative of general formula (IV):

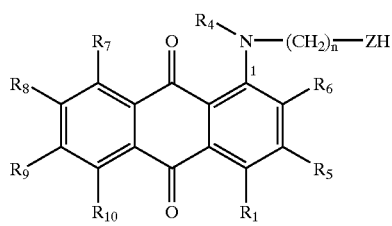

(IV)

in which:

n is between 1 and 20;

Z represents NH or O;

$R_1$, $R_5$, $R_6$, $R_7$, $R_8$, $R_9$ and $R_{10}$, which may be identical or different, each represent a hydrogen atom, a halogen atom, a linear or branched, saturated or unsaturated $C_{1-8}$ hydrocarbon-based group, a hydroxyl group,

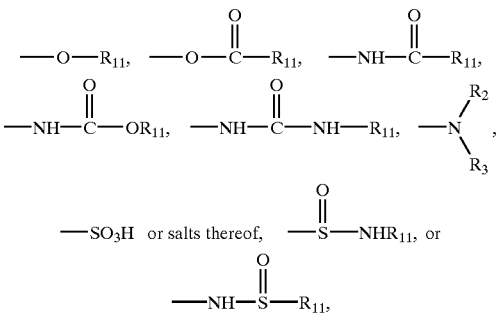

and $R_2$, $R_3$, $R_4$ and $R_{11}$, which may be identical or different, each represent a hydrogen atom, a linear or branched, saturated or unsaturated, optionally hydroxylated $C_{1-8}$ hydrocarbon-based group;

with phosgene or a phosgene derivative at a temperature from 0 to about 160° C. for about 30 minutes to about 20 hours in the presence of a solvent and optionally a base.

7. The process of claim 6 wherein the derivative is carbonyldiimidazole.

8. The process according to claim 6 wherein the solvent is a dipolar aprotic solvent.

9. The process according to claim 6, wherein the solvent is N,N-dimethylacetamide or N,N-dimethylformamide.

10. The process according to claim 6, wherein the base is pyridine, a pyridine derivative, triethylamine or diisopropylethylamine.

11. The process according to claim 4, wherein the solvent is a dipolar aprotic solvent.

12. The process according to claim 4, wherein the solvent is N,N-dimethylacetamide or N,N-dimethylformamide.

13. The process according to claim 4, wherein the base is pyridine, a pyridine derivative, triethylamine or diisopropylethylamine.

14. A process for coloring comprising applying a pigment comprising at least one compound according to claim 11 to a surface to be colored.

15. The process according to claim 14, wherein the compound is 1,3-bis[3-(9,10-dioxo-9,10-dihydroanthracen-1-ylamino)propyl]urea or 1,3-bis[3-(4-methylamino-9,10-dioxo-9,10-dihydroanthracen-1-ylamino)propyl]urea.

16. A cosmetic composition comprising a pigment, the pigment being at least one compound according to claim 1.

17. A cosmetic composition comprising, in a cosmetically acceptable medium, at least one compound according to claim 1.

18. The composition according to claim 17, wherein the compound is 1,3-bis[3-(9,10-dioxo-9,10-dihydroanthracen-1-ylamino)propyl]urea or 1,3-bis[3-(4-methylamino-9,10-dioxo-9,10-dihydroanthracen-1-ylamino)propyl]urea.

19. The composition according to claim 17, wherein the compound is present in an amount ranging from 0.01 to 50% by weight.

20. The composition according to claim 19, wherein the compound is present in an amount ranging from 0.1 to 25% by weight.

21. The composition according to claim 17, wherein the cosmetically acceptable medium comprises a suspension, a dispersion, a solution in a solvent, a solution in an aqueous-alcoholic medium, optionally thickened or gelled, an oil-in-water emulsion, a water-in-oil emulsion, a multiple emulsion, a gel, a mousse, an emulsified gel, a dispersion of vesicles, a two-phase lotion, a multiphase lotion, a spray, a free powder, a compact powder, a cast powder or an anhydrous paste.

22. The composition according to claim 17, wherein the composition is in the form of a makeup product for a face or a body or lips or keratin fibres, a skin care product for the face or the body, an antisun composition, an artificial tanning composition or a hair care composition.

* * * * *